(12) United States Patent
Imran

(10) Patent No.: US 8,433,401 B2
(45) Date of Patent: Apr. 30, 2013

(54) RING ELECTRODE ASSEMBLY AND APPLICATIONS THEREOF

(75) Inventor: Mir Imran, Los Altos Hills, CA (US)

(73) Assignee: InCube Labs, LLC, San Jose, CA (US)

( * ) Notice: Subject to any disclaimer, the term of this patent is extended or adjusted under 35 U.S.C. 154(b) by 105 days.

(21) Appl. No.: 12/832,011

(22) Filed: Jul. 7, 2010

(65) Prior Publication Data

US 2011/0009805 A1   Jan. 13, 2011

Related U.S. Application Data

(60) Provisional application No. 61/224,453, filed on Jul. 9, 2009.

(51) Int. Cl.
*A61N 1/30* (2006.01)
(52) U.S. Cl.
USPC .............................. 604/20; 604/19
(58) Field of Classification Search .............. 604/19–22, 604/294
See application file for complete search history.

(56) References Cited

U.S. PATENT DOCUMENTS

| | | | |
|---|---|---|---|
| 5,002,527 A * | 3/1991 | Reller et al. | 604/20 |
| 6,413,255 B1 | 7/2002 | Stern | |
| 2001/0023330 A1 | 9/2001 | Palti | |
| 2006/0089590 A1 | 4/2006 | Higuchi et al. | |
| 2007/0106278 A1 | 5/2007 | Higuchi et al. | |

OTHER PUBLICATIONS

International Search Report, Written Opinion, and Notice of Transmittal of same mailed Feb. 15, 2011 for PCT/US2010/041239.

* cited by examiner

*Primary Examiner* — Nicholas Lucchesi
*Assistant Examiner* — Rebecca E Eisenberg
(74) *Attorney, Agent, or Firm* — Mahamedi Paradice Kreisman LLP

(57) ABSTRACT

A pair of electrodes having a concentric arrangement and a medium. One of the pair of electrodes known as the delivery electrode (typically the inner electrode), is coupled to an electrical current source. The other electrode, known as the floater electrode is electrically isolated from the delivery electrode. The medium is directly or otherwise electrically coupled to one of the electrodes.

26 Claims, 2 Drawing Sheets

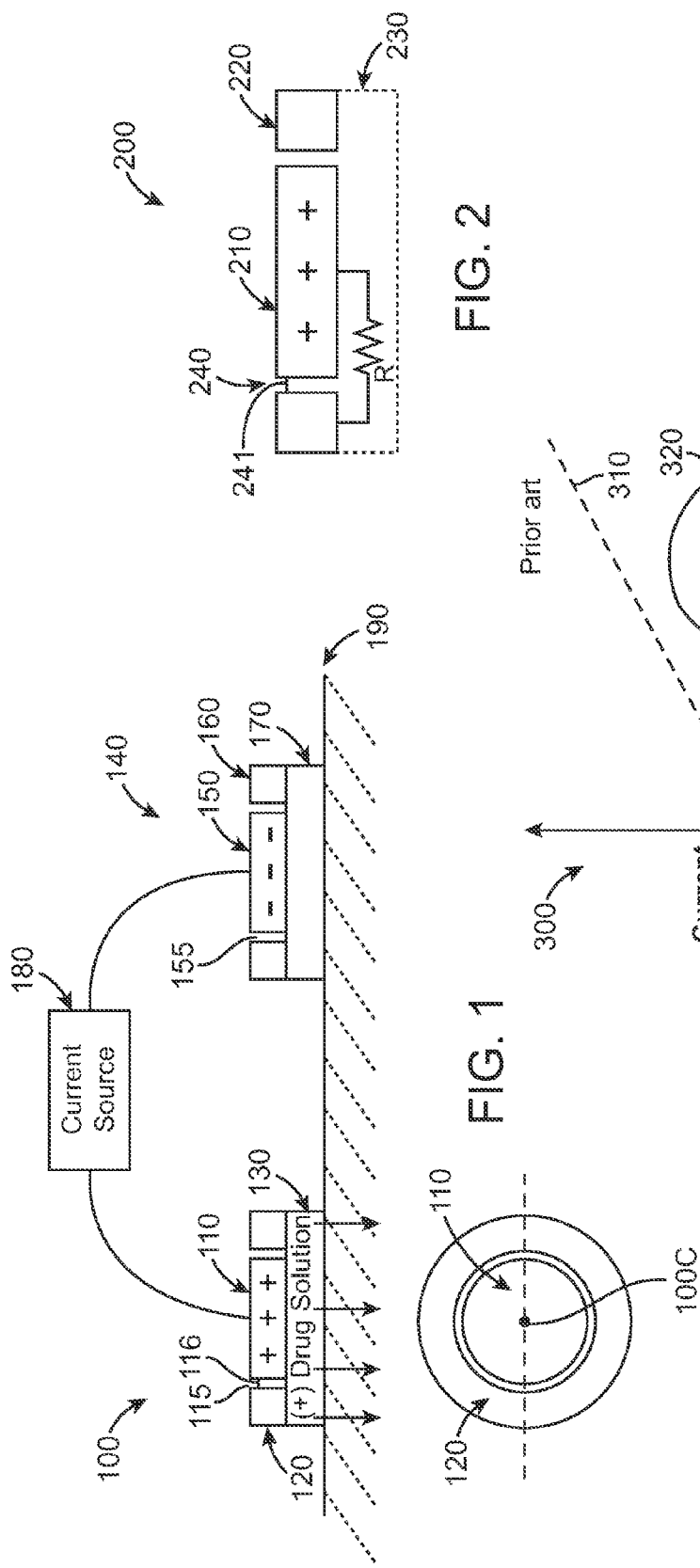
FIG. 1
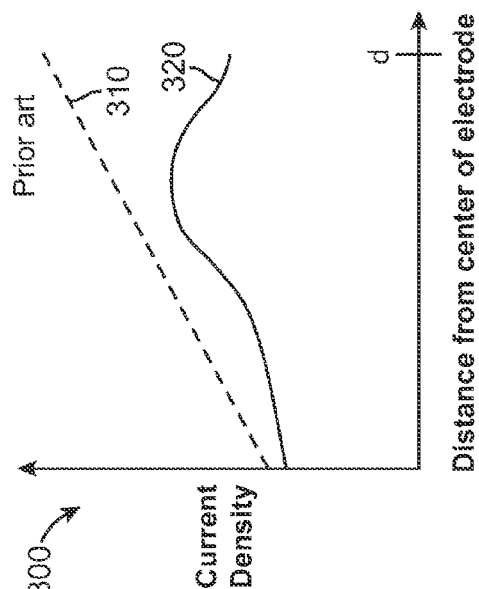
FIG. 2
FIG. 3

RING ELECTRODE ASSEMBLY AND APPLICATIONS THEREOF

RELATIONSHIP TO OTHER APPLICATIONS

This application claims the benefit of priority to Provisional U.S. Patent Application No. 61/224,453, entitled "RING ELECTRODE DEVICE AND APPLICATIONS THEREOF", filed Jul. 9, 2009; the aforementioned priority application being hereby incorporated by reference for all purposes.

FIELD OF THE INVENTION

Embodiments described herein relate to electrode assemblies for iontophoretic transdermal delivery devices used for the delivery of various therapeutic agents. More specifically, embodiments described herein relate to electrode assemblies for iontophoretic transdermal delivery devices.

BACKGROUND

Electrical devices are commonly used for various medical diagnosis and treatment purposes. One such use is the use of electrodes to carry electric currents to a patient (also referred to herein as a user) for different purposes. Electrodes are conductors through which an electric current can enter or leave a medium. In the medical field, electrodes have been used in part with, for example, defibrillators, electrocardiography ("EKG"), electroencephalography ("EEG"), and iontophoresis.

Iontophoresis is a non-invasive method of propelling high concentrations of a charged substance, known as the active agent, transdermally by repulsive electromotive force using a small electrical charge. The active agent can include a drug or other therapeutic agent for example, insulin, iron containing compounds, chemotherapeutic agents, etc. The charge is applied by an electrical power source (also referred to herein as an electrical current source) to an active electrode assembly placed on the skin which contains a similarly charged active agent and a solvent in which it is dissolved. Current flows from the electrode assembly through the skin and then returns by means of a return or counter electrode assembly also placed on the skin. A positively charged electrode assembly, termed the anode will repel a positively charged active agent, or anion, into the skin, while a negatively charged electrode assembly, termed the cathode, will repel a negatively charged active agent, known as a cation into the skin.

When the electrode assemblies are placed on the skin, the electric field lines from the electrode assemblies go through the skin. This causes a large amount of electric field crowding near the edges of the electrodes and leads to a higher current density along the edges of the electrode along with ohmic heating of the edges and/or skin in electrical contact with the edges due to the higher current density. This phenomenon is known as edge effect. As a result, when a sudden amount of current is passed to the electrodes, the edges of the electrodes may heat and cause burns or other thermal injury on the user's skin. Therefore, there is a need for electrode assemblies that distribute current density more evenly so that the edge effect and the accompanying heating produced by the edge effect may be reduced.

BRIEF DESCRIPTION OF THE DRAWINGS

FIG. 1 illustrates an embodiment of a iontophoretic transdermal delivery system having an electrode assembly for reducing edge effects.

FIG. 2 illustrates an equivalent circuit diagram of an embodiment of an electrode assembly having two electrodes for reducing edge effects.

FIG. 3 is a line graph illustrating the difference between the prior art and an embodiment of the electrode assembly for reducing edge effects.

DETAILED DESCRIPTION

Figure 4:
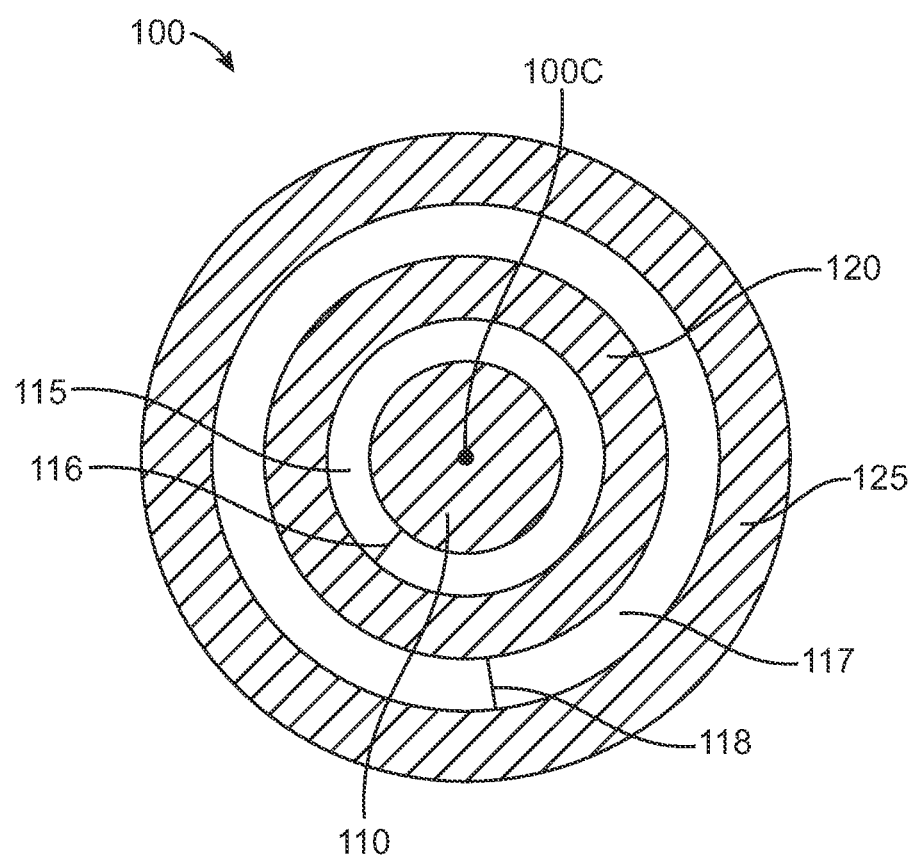
FIG. 4 illustrates an embodiment of an electrode assembly having three electrodes for reducing edge effects.

Various embodiments described herein provide ring electrode assemblies for use with various transdermal applications including iontophoretic transdermal delivery devices, though other applications are also contemplated. Such embodiments are particularly useful for reducing edge effects and accompanying thermal injury occurring during the delivery of current to the skin. In many embodiments, the electrode assembly comprises a pair of electrodes having a concentric arrangement and a medium. One of the pair of electrodes known as the delivery electrode (typically the inner electrode), is coupled to an electrical current source. The other electrode, known as the floater electrode is electrically isolated from the delivery electrode. The medium is directly or otherwise electrically coupled to one of the electrodes. The medium will typically comprise an aqueous solution comprising an electrically charged active agent such as ionic iron that is dissolved in the medium and is transported into the skin though use of a current delivered to the skin from one of the pair electrodes known as the delivery electrode. In various embodiments, the solution or other medium can be at least partially contained in a porous mesh or other porous matrix.

In many embodiments, the pair of electrodes comprises a disk and a ring, and are concentrically arranged so that the pair of electrodes substantially share the same center. A concentric arrangement is defined as an arrangement such that the middle or center of one of the pair of electrodes is positioned near the middle or center of the other electrode.

Among other applications and/or benefits, various embodiments of a ring electrode assembly may be used to attenuate the edge effect of the electrode assembly by distributing the current density more evenly over the electrode assembly. In one embodiment, the ring electrode assembly comprises an inner electrode surrounded by an outer (ring) electrode that partially overlays the medium carrying an active agent. As discussed above, because the active agent is typically, a charged substance, the medium carrying the active agent has a conductivity and resistivity.

In many embodiments, the ring electrode assembly includes a gap between the inner electrode and the outer electrode so that the outer electrode is floating (i.e., it is not electrically connected to the inner electrode or to a current source). However, due to the conductivity and the resistivity of the active agent in the medium, there is a circumferential resistivity, R, that acts as an electrical connection between the inner electrode and the outer electrode. As a result, when the inner electrode receives electric current directly from a current source, the outer electrode may receive a portion of the electric current from the inner electrode. This causes less current to be driven along the edges of the inner electrode and reduces the edge effect. Consequently, the current density becomes more evenly distributed on the surface of the electrode assembly. According to an embodiment, the arrangement of the inner electrode and the outer electrode attenuates the edge effect on the inner electrode to prevent burns or other thermal injury on a user's skin.

FIG. 1 illustrates an embodiment of an electrode assembly useful for transdermal iontophoresis. In one embodiment, the system comprises a first electrode assembly 100, a second electrode assembly 140 and a current source 180. The iontophoresis system of FIG. 1 shows the first electrode assembly 100 and the second electrode assembly 140 attached to the skin 190 of a user. In this embodiment, the first electrode assembly 100 and the second electrode assembly 140 each comprise a disk shaped inner electrode and a ring (circular) shaped outer electrode. However other shapes are also contemplated for both the inner and outer electrodes. For example, the inner electrode can be oval shaped and the outer electrode may have an oval ring shape. Also, the perimeter of the inner and/or outer electrode may have over-layed sinusoidal pattern individually or collectively. The two sinusoidal patterns can be in phase or 180 out of phase to further reduce edge effects depending upon one or more factors (e.g., drug, skin type, electrode, AC current frequency, etc.).

The first electrode assembly 100 comprises an inner electrode 110, surrounded by an outer electrode 120. Typically, outer electrode 120 will surround all of inner electrode 110, but in some embodiments it may only surround only a selected portion (e.g., half or three quarters of the perimeter) of inner electrode 110. The inner electrode 110 and the outer electrode 120 can have a concentric arrangement so that they share the same center 100C. However, non-concentric arrangements are also contemplated. In many embodiments, there is a gap 115 between the inner electrode 110 and the outer electrode 120. As a result, the outer electrode 120 is floating and is not in electrical contact with the inner electrode 110. The width 116 of gap 115 can be selectable based on several factors described herein. For example, gap width 116 can be increased for higher frequencies. The inner electrode 110 and the outer electrode 120 also partially overlays a medium 130 carrying an active agent. In various embodiments, the medium can comprise an aqueous or other solution in which the active agent is dissolved. In many embodiments, the medium can be at least partially contained in a porous mesh or other porous matrix (not shown) which contacts the skin and is electrically coupled to the power (current) source. Gap width 116 can also be related to the conductivity of the medium, for example it may be proportional to medium conductivity or other electrochemical property (e.g., pH, ionic concentration(s)). Suitable porous matrices can comprise compressed cotton or other fibrous meshes such as meshes made from various polymer fibers. A portion of the medium may also be contained in a reservoir (not shown) which is electrically coupled to the power source. In some embodiments, the user and/or medical provider may select from a number of inner and outer electrode shapes and sizes so that gap width 116 can be selected by the user and/or medical provider depending upon one or more factors such as the particular drug or other active agent and/or user skin type or property (e.g., color, dryness, amount of sun exposure etc). In one approach, this can be achieved by allowing the user to select from a variety of preconfigured/prepackaged electrode assemblies having particular inner and outer electrode shapes (e.g., disk and ring shaped) and sizes and corresponding gap widths. In another approach, this can be achieved by packaging an electrode assembly kit (not shown) including an array of inner and outer electrode shapes and sizes where the user can assemble the electrode assembly with particular sized and shape inner and outer electrodes (e.g., disk and ring shaped) to achieve a particular gap width. The kit would include instructions for selecting particular electrodes (depending upon factors such as drug, skin type and property) and assembling them into electrode assembly 110.

The active agent can comprise one or more ionic drugs or other ionic agents having an ionic charge of a selected polarity (e.g. positive) when dissolved in the medium. In many embodiments the active agent comprises a salt which dissociates into its ionic components when dissolved in the media. In particular embodiments the active agent can comprise ionic iron from a dissociated ferrous salt or a charged chelated iron complex such as ferro-pyrophosphate.

The active agent found in the medium 130 can be transported through the skin 190 once the inner electrode 120 receives an electric current from the current source 180 that has the same polarity as the agent. In some embodiments, the current from the source 180 may alternate in polarity, so that durations in which the current output induces delivery of the agent from the electrode assembly is intermittent or alternating.

The system further comprises a second electrode assembly 140 coupled to the current source 180. In one embodiment, as discussed above with respect to the first electrode assembly 100, the second electrode assembly may also comprise an inner electrode 150 and an outer electrode 160. In one embodiment, the second electrode assembly 140 may not deliver the active agent, but rather, act as a return electrode assembly for the electric current. As a return electrode, the second electrode assembly may be simplified (e.g. without ring arrangement), or substantially duplicate the arrangement of the first electrode assembly.

In another embodiment, the second electrode assembly 150 may also provide a medium 170 that contains an active agent to be administered to a user's skin 190. In such an embodiment, the inner electrode 150 receives current from the current source 180 and may induce a charged active agent with the same polarity to be transported from medium 170 into the skin 190. Furthermore, in various embodiments, there is a gap 155 between the inner electrode 150 and the outer electrode 160. The width of gap 155 can be selectable using one or more factors described herein.

The current source 180 can provide either a direct current or an alternating current. For alternating current embodiments, delivery of the active agent from the respective first and (optionally) second electrode assemblies may also alternate. For example, in one embodiment, the system may provide to a user drugs or other therapeutic agents bearing a positive ionic charge (e.g., ionic iron) in the medium 130 of the first electrode assembly 100 and drugs or other therapeutic agent bearing a negative ionic charge in the medium 170 of the second electrode assembly 140. When the current source 180 provides an alternating current to the first electrode assembly 100 and the second electrode assembly 140, the respective agent (e.g., drugs) may be transferred from both mediums in an alternating fashion.

FIG. 2 illustrates an equivalent circuit diagram of an embodiment of an electrode assembly 200 having an inner and outer electrode 210 and 220 respectively. As discussed above with reference to FIG. 1, in one embodiment, the electrode assembly 200 may be in the shape of a disk with inner electrode 210 having a substantial disk shape and the outer electrode 220 having a substantial ring shape. The inner electrode 210 and the outer electrode 220 may have a concentric arrangement so that they share the same center. Like the electrode assembly in FIG. 1, the electrode assembly 200 comprises an inner electrode 210, an outer electrode 220, and a medium 230 for carrying an active agent. As discussed above, because this active agent bears an ionic charge, the medium 230 is both conductive and resistive. As a result, there is a circumferential resistance, R, between the inner electrode 210 and the outer electrode 220. This circumferential resistance, R, will vary depending on the conductivity and resistivity of the active agent found in the medium 230 as well as other factors.

In one embodiment, there is a gap 240 (having a width 241) between the inner electrode 210 and the outer electrode 220 so that the outer electrode 220 is floating. However, due to the conductivity and the resistivity of the active agent in the medium 230, the circumferential resistivity, R, acts as an electrical connection between the inner electrode 210 and the outer electrode 220. As a result, when the inner electrode 210 receives electric current directly from a current source (not shown in FIG. 2, but similar to the current source 180 in FIG. 1), the outer electrode 220 may receive a portion of the electric current from the inner electrode 210 (e.g., depending upon factors such as gap width and the conductivity, resistivity of the active agent and like properties). This causes less current to be driven along the edges of the inner electrode 210 and thus reduces the edge effect. Consequently, the current density becomes more evenly distributed on the surface of the electrode assembly 200. According to an embodiment, the arrangement of the inner electrode 210 and the outer electrode 220 attenuates the edge effect on the inner electrode 210 to prevent burns or other thermal injury to the user's skin. Depending upon one or more factors (such as the active agent, skin type and frequency of the current source) gap width 241 can be selected to drive increased amounts or proportions of current to the outer electrode 220 and thereby reduce edge effects. In some embodiments, depending upon one or more of the previously described factors, this can be achieved through increased gap widths.

In the embodiment described above, the inner electrode 210 and the outer electrode 220 share the same center so that there is a gap 240 between the outer wall of the inner electrode 210 and the inner wall of the outer electrode 220. The size of the gap 240, as other embodiments of gaps (described herein) can be determined by, at least in part, the conductivity of the active agent in the medium 230. For example, the lower the conductivity of the active agent, the smaller the gap size. The relationship between gap size and agent conductivity may be linear, geometric, logarithmic with other relationships contemplated. The size or width 241 of the gap 240 can also be selectable based on several other factors such as the resistance of the user's skin, and the frequency, amplitude, shape or other characteristic of the current supplied by the current source. For example, for use of an AC current source, the gap width can be increased for higher frequencies of the AC current.

FIG. 3 is a line graph illustrating the difference between the prior art and an embodiment of the electrode assembly. The line graph 300 displays the current density of an electrode assembly with respect to the distance from the center of the electrode assembly. The prior art is displayed with a hashed line 310. The current density of the prior art's electrode assembly increases as the distance from the center of the electrode assembly increases. In this example, the distance, d, represents the edge of the electrode assembly. The line graph 300 shows the edge effect of the prior art because the current density of line 310 is highest at the distance, d.

In contrast, the curved line 320 represents the current density, with respect to distance (from the center of the electrode), of an embodiment of the electrode assembly having an inner electrode and an outer ring electrode. As the distance from the center increases, the current density first increases, but begins to level out. Curved line 320 shows that the current density is more evenly distributed across the inner electrode resulting in an attenuation of the edge effect and in turn, no substantial increase in current density (e.g., no more than about 25%, more preferably no more than about 10%) from the center of the inner electrode to the edges of the electrode assembly. In use, such embodiments not only reduce edge effects, but also serve to decrease any temperature increase at or near the electrode edges due to edge effects.

According to another embodiment shown in FIG. 4, electrode assembly 100 may comprise a third outer electrode 125 arranged and configured to further reduce edge effects on the electrode assembly. Adding a third outer electrode may result in even more even distributions of the current density than from a second electrode 120. Like the second electrode 120 discussed above in FIG. 1, third outer electrode 125 may surround all or a portion, of both the inner electrode 110 and electrode 120 (now middle electrode 110) and may be separated from middle electrode 120 by a gap 117 having a width 118 selectable according to one or more factors described herein (e.g., the drug and conductivity of the medium, skin type etc.). All three electrodes can have a concentric arrangement, though eccentric arrangements are also contemplated. In one embodiment, inner electrode 110 can be disk shaped and electrodes 120 and 125 can be ring (circular shaped). In another embodiment, inner electrode 110 is disk shaped, middle electrode 120 is ring shaped and outer electrode 125 has an oval ring shape. Other shapes and arrangements are also contemplated such as the use of oval ring shapes for one or both of electrodes 120 and 125.

CONCLUSION

The foregoing description of various embodiments of the invention has been presented for purposes of illustration and description. It is not intended to limit the invention to the precise forms disclosed. Many modifications, variations and refinements will be apparent to practitioners skilled in the art. For example, various embodiments of the invention contemplate multiple pairs of concentrically arranged electrodes. Alternatively, the electrode pair or other numbers of electrodes may have an eccentric arrangement. Also, the electrode assembly can be sized, shaped and otherwise configured for a variety of biomedical applications including transdermal iontophoretic drug delivery (both pediatric and adult applications) as well as various sensor and stimulating electrode applications, for example, for use in electromyogram, EEG and EKG and like applications.

Elements, characteristics, or acts from one embodiment can be readily recombined or substituted with one or more elements, characteristics or acts from other embodiments to form numerous additional embodiments within the scope of the invention. Moreover, elements that are shown or described as being combined with other elements, can, in various embodiments, exist as standalone elements. Hence, the scope of the present invention is not limited to the specifics of the described embodiments, but is instead limited solely by the appended claims.

What is claimed is:

1. An electrode assembly for reducing edge effects during the transdermal ionotphoretic delivery of an active agent, the assembly comprising:

a pair of electrodes for delivering current to the skin, the pair of electrodes comprising an inner and outer electrode having a concentric arrangement, the concentric arrangement including a gap between the inner electrode and outer electrode such that the outer electrode is electrically isolated from the inner electrode, the pair of electrodes configured to be coupled to an electrical current source; and a medium for carrying an active agent, the medium being positionable to be adjacent to a skin layer of a user so that application of current to the electrode assembly causes the active agent from the medium to be transported through the skin layer; and wherein when the medium is positioned between the inner electrode and the outer electrode, the concentric arrangement of the pair of electrodes is configured to allow a current to flow through the medium from the inner electrode to the outer electrode to reduce current being driven along an edge of the inner electrode.

2. The assembly of claim 1, wherein the pair of electrodes comprise substantially the same material.

3. The assembly of claim 1, wherein the size of the gap is proportional to an amount of current provided by the electrical current source.

4. The assembly of claim 1, wherein the size of the gap is proportional to the frequency of the current source.

5. The assembly of claim 1, wherein the size of the gap is related to the conductivity of the medium.

6. The assembly of claim 5, wherein the size of the gap is proportional to the conductivity of the medium.

7. The assembly of claim 1, wherein the inner electrode has a substantial disk shape.

8. The assembly of claim 1, wherein the outer electrode has a substantial ring shape.

9. The assembly of claim 1, wherein the electrode assembly further comprises a third electrode.

10. The assembly of claim 9, wherein the third electrode is concentrically arranged with respect to the inner electrode and the outer electrode, such that the third electrode is not in contact with the inner electrode or the outer electrode.

11. The assembly of claim 1, wherein the active agent comprises an ionic agent, an ionic drug, an ionic compound or ionic iron.

12. The assembly of claim 1, wherein the inner electrode and the outer electrode are arranged such that when current is applied to the electrode assembly, a current density along an edge of the inner electrode is not substantially increased with respect to a center of the inner electrode.

13. The assembly of claim 1, wherein the inner electrode and the outer electrode are arranged such that when current is applied to the electrode assembly, a portion of the current flows through the outer electrode so as to reduce current density along an edge of the inner electrode.

14. A system for reducing edge effects during the transdermal ionotphoretic delivery of an active agent, the system comprising:
a pair of electrode assemblies, wherein at least one of the electrode assemblies comprises a pair of electrodes comprising an inner and outer electrode having a concentric arrangement the inner electrode being electrically isolated from the outer electrode;
a medium for carrying an active agent, the medium being positioned to be adjacent to a skin layer of a user so that application of current to the pair of electrode assemblies causes the active agent from the medium to be transported through the skin layer and wherein when the medium is positioned between the inner electrode and the outer electrode, the concentric arrangement of the inner and outer electrodes is configured to allow current to flow through the medium from the inner electrode to the outer electrode; and
a current source to deliver current to the pair of electrode assemblies.

15. The system of claim 14, wherein the inner electrode and the outer electrode are arranged such that when current is applied to electrode assemblies, the current density along an edge of the inner electrode is not substantially increased with respect to a center of the inner electrode.

16. The system of claim 14, wherein the inner electrode and the outer electrode are arranged such that when current is applied to the electrode assembly, a portion of the current flows through the outer electrode so as to reduce current density along an edge of the inner electrode.

17. The system of claim 14, wherein a concentric arrangement of the electrodes includes a gap between the inner electrode and outer electrode.

18. The system of claim 17, wherein the size of the gap is proportional to the frequency of the current source.

19. The system of claim 17, wherein the size of the gap is related to the conductivity of the medium.

20. The assembly of claim 19, wherein the size of the gap is proportional to the conductivity of the medium.

21. The system of claim 14, wherein the inner electrode has a substantial disk shape.

22. The system of claim 21, wherein the outer electrode has a substantial ring shape.

23. The system of claim 14, wherein the first electrode assembly further comprises a third electrode.

24. The system of claim 23, wherein the third electrode is concentrically arranged with respect to the inner electrode and the outer electrode, such that the third electrode is not in contact with the inner electrode or the outer electrode.

25. The system of claim 14, wherein the active agent comprises an ionic agent, an ionic compound or ionic iron.

26. The system of claim 14, wherein both of the electrode assemblies each comprise a pair of electrodes comprising an inner and outer electrode having a concentric arrangement.

* * * * *